United States Patent
Yada et al.

(10) Patent No.: US 7,221,731 B2
(45) Date of Patent: May 22, 2007

(54) X-RAY MICROSCOPIC INSPECTION APPARATUS

(75) Inventors: Keiji Yada, Tokyo (JP); Hiromi Kai, Tokyo (JP); Yasushi Saito, Tokyo (JP)

(73) Assignee: Tohken Co., Ltd., Tokyo (JP)

( * ) Notice: Subject to any disclaimer, the term of this patent is extended or adjusted under 35 U.S.C. 154(b) by 0 days.

(21) Appl. No.: 10/719,887

(22) Filed: Nov. 21, 2003

(65) Prior Publication Data

US 2004/0208280 A1    Oct. 21, 2004

(51) Int. Cl.
G21K 7/00    (2006.01)
(52) U.S. Cl. .................................. 378/43; 250/396 ML
(58) Field of Classification Search ................... 378/43, 378/124, 137, 138; 250/396 ML, 397
See application file for complete search history.

(56) References Cited

U.S. PATENT DOCUMENTS

| | | | | |
|---|---|---|---|---|
| 2,939,954 | A * | 6/1960 | Ong .............................. | 378/43 |
| 3,862,419 | A * | 1/1975 | Veneklasen .................. | 250/306 |
| 4,315,152 | A | 2/1982 | Smith ................... | 250/396 ML |
| 4,544,845 | A | 10/1985 | Michel .................... | 250/396 R |
| 4,629,898 | A | 12/1986 | Orloff et al. ............ | 250/396 R |
| 5,041,732 | A * | 8/1991 | Saito et al. .......... | 250/396 ML |
| 5,044,001 | A * | 8/1991 | Wang ........................... | 378/43 |
| 5,081,656 | A * | 1/1992 | Baker et al. ..................... | 378/4 |
| 5,317,574 | A | 5/1994 | Wang .............................. | 372/5 |
| 5,319,198 | A * | 6/1994 | Wada ........................... | 250/310 |
| 5,602,899 | A | 2/1997 | Larson ........................ | 378/143 |
| 5,832,052 | A * | 11/1998 | Hirose et al. .................. | 378/43 |
| 6,282,263 | B1 | 8/2001 | Arndt et al. ................. | 378/138 |

(Continued)

FOREIGN PATENT DOCUMENTS

DE    100 29 840    1/2001

(Continued)

OTHER PUBLICATIONS

Nixon, W.C., "High-Resolution X-Ray Projection Microscopy," Proc. Roy. Soc., A232, pp. 475-485 (1960).

(Continued)

*Primary Examiner*—Edward J. Glick
*Assistant Examiner*—Chih-Cheng Glen Kao
(74) *Attorney, Agent, or Firm*—Ladas & Parry LLP

(57) ABSTRACT

To provide an X-ray microscopic inspection apparatus capable of performing non-destructive inspection with high resolving power within a very short period, and having advantageous functions such as a high precision electron probe control function, a CT function, an elemental analysis function, and a target switching function. The apparatus includes a magnetic superposition lens having a magnetic field generating portion disposed in the vicinity of an electron generating portion of an electron gun; reflected electron detecting means having a detecting portion disposed above the target for X-ray generation, for detecting a reflected electron from the target; and electron image generating means for performing imaging of a target surface utilizing the signals from the reflected electron detecting means, wherein the apparatus is arranged so that alignment including focus adjustment to the target for X-ray generation and astigmatism correction may be performed based on image information of the electron image. Further, the apparatus is equipped with functions such as the electron probe control function, the CT function, the electron axis alignment function the elemental analysis function, and the target switching function.

1 Claim, 8 Drawing Sheets

U.S. PATENT DOCUMENTS

| | | | |
|---|---|---|---|
| 6,430,254 B2 | 8/2002 | Wilkins | 378/43 |
| 6,555,816 B1* | 4/2003 | Sawahata et al. | 250/310 |
| 6,649,914 B1* | 11/2003 | Moorman et al. | 378/4 |
| 6,882,701 B2* | 4/2005 | Ferrandino et al. | 378/44 |
| 2001/0001010 A1 | 5/2001 | Wilkins | 378/43 |
| 2002/0097834 A1* | 7/2002 | Satoh | 378/46 |
| 2002/0130039 A1 | 9/2002 | Hojoh et al. | 204/275.1 |
| 2003/0039386 A1* | 2/2003 | Ishitani et al. | 382/141 |

FOREIGN PATENT DOCUMENTS

| | | |
|---|---|---|
| EP | 0 473 227 A2 | 3/1992 |
| GB | 735943 | 8/1955 |
| GB | 865050 | 4/1961 |
| GB | 2 131 224 | 6/1984 |
| JP | 2001-138460 | 5/2004 |
| JP | 2004-138460 | 5/2004 |
| WO | 01/15192 A1 | 3/2001 |
| WO | 03/065772 A2 | 8/2003 |

OTHER PUBLICATIONS

Yada, K., et al., "Development of Projection X-Ray Microscopy and Its Biological Applications," *Bulletin of Aomori Public College*, vol. 1, pp. 2-13 (1996).

Yada, K., et al., "Development of Soft X-Ray Microscopy," *Biophysics*, vol. 33, No. 4, pp. 8-16 (1980).

Yada, K., et al., "High-Resolution Projection X-Ray Microscopy," *Multidimensional Microscopy*, Chapter 8, pp. 133-150 (1994).

U.S. Appl. No. 10/719,008, filed Nov. 21, 2003, Yada et al.

Delong, A., et al., "A New Design Of Field Emission Electron Gun With A Magnetic Lens," *Optik*, vol. 81, No. 3, pp. 103-108 (1989).

Mayo, S.C., et al., "X-Ray Phase-Contrast Microscopy and Microtomography," *Optics Express*, vol. 11, No. 19, pp. 2289-2302 (Sep. 2, 2003).

Yada, K., et al., "Projection X-Ray Shadow Microscopy Using SEM," *Bulletin of the Research Institute for Scientific Measurements*, Tohoku University, vol. 29, No. 1, pp. 25-42 (1980).

* cited by examiner

X-RAY MICROSCOPIC INSPECTION APPARATUS

BACKGROUND OF THE INVENTION

1. Field of the Invention

The present invention relates to an X-ray inspection apparatus, and specifically, to an X-ray microscopic inspection apparatus with ultra-high resolving power using an electron source for emitting a high brightness electron, to which new functions such as a CT (computerized tomography: X-ray tomography) function with high resolving power never before possible, an elemental analysis function utilizing a fluorescent X-rays, a target switching function capable of selecting a target depending on a purpose of inspection with a plurality of metal targets are added.

2. Description of the Related Art

As an inspection apparatus utilizing an X-ray, various kinds of industrial inspection apparatuses such as an X-ray microscope, a foreign body inspection apparatus, a fluorescent X-ray analyzing apparatus, and medical X-ray apparatuses such as an X-ray diagnostic apparatus are known. FIG. 1 shows a construction example of a conventional X-ray inspection apparatus. The X-ray inspection apparatus in this example is designed so as to obtain a micro X-ray point source 23a by accelerating electrons Re from an electron source 21b by applying a high voltage between a grid 21a and an anode 21c using a thermionic emission cathode 21b as the electron source, and then focusing the electrons Re on a target 23 formed of a thin plate of high-melting point metal such as tungsten by electron lenses 22. Subsequently, the inside of a sample (object to be inspected) 10 is projected in magnification mode by using the point-form X-ray Rx generated from the X-ray target 23a and the microstructure inside of the sample is subjected to non-destructive perspective inspection.

In the conventional X-ray microscopic inspection apparatus that the applicant has developed and commercialized, a two-stage reduction system using lenses having as small spherical aberration and chromatic aberration as possible for the focusing lens system and a $LaB_6$ (lanthanum hexaboride) cathode having an advantageous character as a thermionic source are adopted, and further, an image intensifier with high sensitivity is used, and thereby the resolving power becomes less than 1 μm and achieves about 0.4 μm. This resolving power is the highest value on a global basis as a practical X-ray inspection apparatus at present (the degree of 0.1 μm is the highest value if the exposure time is neglected), and the value may be assumed as the technical limit under the present circumstances. Therefore, the resolving power better than 0.1 μm expected in the invention can not be implemented by the conventional technology (see the following description of the non-patent documents).

On the other hand, several companies have become to add a micro CT function to these X-ray inspection apparatuses, recently, and an arbitrary cross sectional CT images of a sample can be observed, and thereby, its utility has been very much increased. However, the resolving power of a CT image in the present circumstances is several times worse than that of the original projection image, and its development is being inhibited. This is caused by the technical limit of axial runout in the rotation of the sample, which is required to obtain the CT image and essential limit that the sample can not be rotated in the state in which the sample is close to the target.

Conventionally, in the X-ray inspection apparatus of projection type, the kind of sample is only estimated from the image contrast (i.e., difference of transmittance) and the need for the elemental analysis has been extremely great, however, the analysis has been never performed. This is caused by that, if the conventional detector for elemental analysis is disposed underneath the sample, the continuous X-rays directive from the target and the characteristic X-rays from the sample (in this case, fluorescent X-rays) are superposed and can not be distinguished. In addition, as shown in FIG. 1, this is also caused by that there is no space for the accommodation of the detector above the sample 10.

It is necessary to perform observation by changing the way of providing contrast according to the sample, and thus, it is desirable that the accelerating voltage and the kind of target are changed. Changing the accelerating voltage is often performed, however, since it is very difficult to change the target while keeping it in high vacuum and there is no choice but to lead a large scaled apparatus for interchangeable targets, it has never been performed in the conventional X-ray inspection apparatus on-line.

Hereinafter, the conventional technology concerning the resolving power of the X-ray inspection apparatus will be described.

The technology concerning the resolving power is disclosed in Non-patent Document 1, Nixon, "High-resolution X-ray projection microscopy", 1960, A232: pp. 475–485, Non-patent Document 2, Keiji Yada & Hisashi Ishikawa, "Transmission X-ray Shadow Microscopy using SEM", Bulletin of the Research Institute for Scientific Measurements, Tohoku University, 1980, Vol. 29, No. 1, pp. 25–42, Non-patent Document 3, Keiji Yada & Kunio Shinohara, "Development of Soft X-ray Microscopy", 1980, Biophysics, Vol. 33, No. 4, pp. 8–16, Non-patent Document 4, Keiji Yada & Shoichi Takahashi, "High-Resolution Projection X-ray Microscopy", 1994, Chap. 8, pp. 133–150, and Non-patent Document 5, Keiji Yada & Kunio Shinohara, "Development of Projection X-Ray Microscopy and Its Biological Applications" 1996, Bulletin of Aomori Public College, Vol. 1, pp. 2–13, for example. In Non-patent Document 1, there described that, regarding X-ray Shadow Microscopy, the limit of its resolving power has been 0.5 μm conventionally, however, the resolving power of 0.1 μm is achieved by using a high brightness electron emitter and a very thin metal film (0.1 μm in thickness) as the target at this time. In addition, there also described that the exposure time for obtaining a sheet of image is five minutes, and after Non-patent Document 1 is disclosed, studies for shortening the exposure time have been actively performed. Further, Non-patent Document 2 is a research report (bulletin of the research institute for scientific measurements, Tohoku University) on the projection X-ray shadow microscopy utilizing an irradiation system of an electron microscope, and there described that the resolving power of 0.1 μm is achieved. Additionally, theoretical analyses are performed regarding respective factors that affect the resolving power, and there derived the conclusion that the spot size of the X-ray source exerts the greatest effects on the resolving power. Furthermore, there described that, by utilizing the microscope as a SEM (scanning electron microscope), swinging the electron beam with a deflection coil is utilized for focusing.

Moreover, Non-patent Document 3 is for explaining the trend in the X-ray microscopy to the present, and there explained that the soft X-ray microscope of a relatively short wavelength (0.1 to 10 nm) by specifically referring to the observation of biological samples. The contents of Non-patent Document 4 are substantially the same as those of Non-patent Document 2, however, there shown a densitometry profile of an X-ray image having the resolving power of 0.1 μm (on 146 page in the main body). Non-patent Document 5 is for explaining the X-ray microscope in an easily understandable way, and there described that the image quality becomes better by changing the target in relation to the sample that is difficult to provide contrast as is the case with Non-patent Documents 2, 3, and 4.

The current semiconductor technology is ever being directed to miniaturization, and the X-ray microscopic apparatus of resolving power on the order of 0.1 μm is expected to become essential in the near future. The nano-technology extends across information, medical, environmental fields, and, for example, in a micromachine referred to in the medical field, the component constituting the machine becomes smaller than 1 μm and ready to enter nano order. In addition, the current semiconductor technology is ever being directed to miniaturization, and non-destructive inspection in the class of the resolving power equal to or better than 0.1 μm using the micro X-ray source never before possible becomes a challenge that is required by all means. Especially, in the information field, there is the great challenge that the line width in the next generation very large scale integrated circuit is to be made from 180–130 nm at present to 70–100 nm. Simultaneously, it is often the case where the microstructure consisted principally of a light element become an object to be observed, and, for providing contrast to the image, it becomes an important challenge that the high resolution power is held even in the case of using an X-ray having a long wavelength by the low accelerating voltage of 10 to 20 kV, which is difficult in the conventional X-ray inspection apparatus. Concurrently with that, many new functions never before possible would be desired.

In order to manufacture an X-ray inspection apparatus having high resolution never before possible, an electron source with higher brightness (greater electron current per unit area/unit solid angle) and greater emission current amount becomes required. Additionally, an electron lens system for assuring as a great electron probe current amount as possible becomes also required. Further, devices for increasing the heat release effect of the target become required so that the target may not melt or evaporate even if an electron probe having such high current density impinges thereon.

The first of new functions that are desired to be put into practical use in the X-ray inspection apparatus having ultra-high resolving power (here, resolving power of equal to or better than 0.1 μm is referred to) is a function (hereinafter, referred to as focal point adjustment function) capable of easily performing adjustment such as focus adjustment to the target (X-ray source) for X-ray generation of the electron probe and astigmatic correction of the electron probe while watching the image. Further, the second is a function (hereinafter, referred to as electron probe control function) of swinging the electron probe freely on the target surface so that the choice of suitable target may be enabled. The third is an electron axis alignment function capable of easily performing axis alignment of the electron beam allowed to impinge on the target for X-ray generation. The fourth is a CT function with high resolving power at high speed. The fifth is an elemental analysis function for analyzing the element of the desired part of the perspective image. For this, the elemental analysis with a fluorescent X-ray is utilized, and the X-ray target therefor is necessary. Therefore, the sixth function is, with a plurality of targets for short wavelengths and long wavelengths provided other than the target for analysis, a target switching function capable of choice of suitable target depending on the purpose of inspection.

The invention is achieved in light of the above described circumstances, and an object of the invention is to provide an X-ray microscopic inspection apparatus capable of largely contributing to the nano-technology fields. Specifically, the object of the invention is to provide an X-ray microscopic inspection apparatus capable of performing non-destructive inspection with high resolving power within a very short period, and equipped with advantageous functions such as the high precision electron probe control function, the CT function, the elemental analysis function, and the target switching function.

SUMMARY OF THE INVENTION

The invention relates to an X-ray microscopic inspection apparatus having X-ray generating means for generating an X-ray by allowing an electron beam from an electron source to impinge on a target for X-ray generation, for inspecting an object to be inspected by utilizing the X-rays, and the above described object of the invention is achieved by including a magnetic superposition lens having a magnetic field generating portion disposed in the vicinity of an electron generating portion of an electron gun; reflected electron detecting means having a detecting portion disposed above the target for X-ray generation, for detecting a reflected electron from the target; and electron image generating means for performing an image of a target surface utilizing the signals from the reflected electron detecting means, wherein the apparatus is arranged so that alignment including focus adjustment to the target and astigmatism correction may be performed based on image information of the electron image.

Further, the invention is achieved by including a magnetic superposition lens having a magnetic field generating portion disposed in the vicinity of an electron generating portion of an electron gun; and a scan coil for freely swinging an electron probe formed via the magnetic superposition lens on a surface of the target for X-ray generation. Furthermore, the invention is achieved by including a magnetic superposition lens having a magnetic field generating portion disposed in the vicinity of an electron generating portion of an electron gun; and an electron beam axis alignment coil disposed in the vicinity of the electron generating portion of said electron source, for aligning an axis of an electron beam allowed to impinge on the target for X-ray generation via the magnetic superposition lens while accelerating the electron. Moreover, the invention is achieved by including an electron probe control means for scanning an electron beam and X-ray CT image generating means for allowing a microstructure of a cross section of interest of the object by processing plural sets of images of transmitted X-rays of the object in response to the scanning.

In addition, the invention is achieved by including a magnetic superposition lens having a magnetic field generating portion disposed in the vicinity of an electron generating portion of an electron gun; fluorescent X-ray detecting means having a detecting portion disposed above the object and outside the X-ray target for detecting fluorescent X-rays generated from the object; and elemental analysis means for analyzing elements of the object based on the fluorescent X-ray signals from the fluorescent X-ray detecting means. Further, the invention is achieved by including a magnetic superposition lens having a magnetic field generating portion disposed in the vicinity of an electron generating portion of an electron gun; and a plurality of targets for different characteristic X-ray generation having different wavelengths, wherein the apparatus is arranged so that characteristic X-rays of a wavelength of interest may be generated by switching the targets depending on a purpose of inspection.

DETAILED DESCRIPTION OF THE PREFERRED EMBODIMENT

First, a basic construction of an X-ray microscopic inspection apparatus according to the invention will be described. In the invention, the apparatus has a construction in which means for realizing multiple functions such as a focal point adjustment function with a reflection electron image, an electron probe control function, an electron axis alignment function, a CT function, an elemental analysis function, and a target switching function, which will be described later, are added to the construction of the X-ray microscopic inspection apparatus having a magnetic superposition lens that will be described hereinafter.

Figure 3:
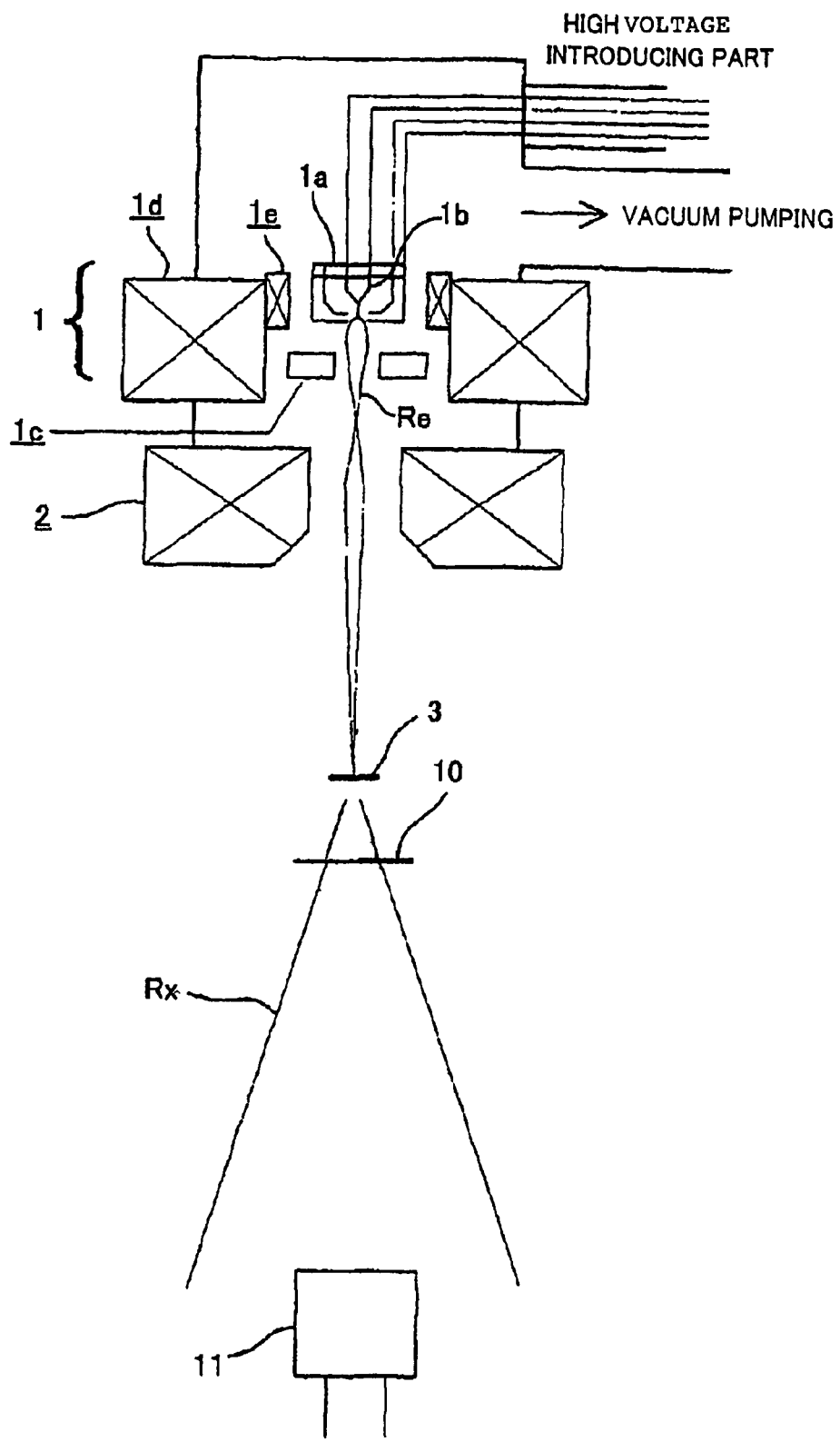
FIG. 3 is a schematic diagram showing an example of a basic construction of an X-ray microscopic inspection apparatus according to the invention.

FIG. 3 shows an example of the basic construction of the X-ray microscopic inspection apparatus according to the invention, and X-ray generating means includes an electron gun 1, an objective lens 2, a target 3, etc., and the electron gun 1 is constituted by a Schottky module 1a, an electron source 1b, an anode 1c, etc.

In the embodiment, a construction is adopted in which a magnetic superposition lens 1d that has never been used for the X-ray microscope is disposed in the vicinity of the electron generating portion of the electron gun 1 of the X-ray microscopic inspection apparatus, and, by superposing the magnetic field formed by the magnetic superposition lens 1d on the electric field formed by the electron gun at least from the electron generating portion 1a to the anode 1c as a component element of electron accelerating means, the electrons Re are focused while accelerating them by the anode 1c. That is, the electron beam loss amount of the focused electron beam is reduced by accelerating the electron Re just after generated from the electron generating portion 1a while focusing them. Then, the focused electron beam (electron probe for X-ray generation) having high current density is allowed to impinge on the target 3 so as to increase the X-ray amount generated from the target 3.

The so-called magnetic superposition lens has been conventionally used in an electron beam apparatus such as a transmission electron microscope and a scanning electron microscope, however, the lens can not be applied to the X-ray microscopic inspection apparatus because the spot diameter of the electron beam is small in these electron beam apparatuses, but the desired X-ray amount can not be obtained on the target 3 because of the small emission current amount. The reason for that is, in the electron microscope, the small emission current amount is not problematic to such an extent because it is enough for the signal amount, however, in the X-ray microscopic inspection apparatus, different from the electron microscope, the problem that the X-ray image is dark and long exposure time is needed raises with the small amount of the probe current. Especially, short exposure time is a required condition for the widespread for industrial use. Further, the electron beam apparatus such as an electron microscope has the construction in which a magnetic circuit etc. is incorporated within the electron gun chamber that requires ultra-high vacuum. In the X-ray microscopic inspection apparatus that requires greater electron flow (probe current), it has been difficult to solve the vacuum deterioration due to the magnetic circuit accompanying gas and heat generation that is emitted by the electron flow impingement. On this account, there is no example in which the lens used in the electron beam apparatus is applied to the X-ray inspection apparatus, and, in the conventional X-ray inspection apparatus, the electron beam accelerated by the anode has been focused by bending it by the lens. In the X-ray microscopic inspection apparatus according to the invention, the problem is solved by adopting a material that is thought to emit small amount of gas, by disposing the magnetic circuit outside the vacuum with water cooling of the circuit.

Hereinafter, the construction of the magnetic superposition lens that is unique to the X-ray inspection apparatus according to the invention will be described by comparison with the lens used in the electron beam apparatus such as a scanning electron microscopic apparatus.

The FE (field emission) electron gun provides electron beams having high brightness and good coherence, and thereby, demonstrates its high performance in a transmission electron microscope, a scanning electron microscope, a scanning transmission electron microscope, an electron beam exposure apparatus, etc. However, this performance is obtained by reducing the crossover of the electron source extremely small. The so-called electron beam probe demonstrates its performance only when the probe is made in a size equal to or less than nanometer (sub-nanometer). However, in order to obtain a probe in which the crossover of the electron source is enlarged from submicron to micron size, it becomes difficult to obtain sufficient probe current due to the large aberration of the magnification lens. This aberration is associated with the distance from the position of the electron source of the electron gun to the first stage of the magnification lens (single stage or plural stages), and proportional to the third to fourth power of the distance. Therefore, a so-called compound lens in which an electron lens is added to the electron gun part is devised and put into practical use in some quarters.

Figure 2:
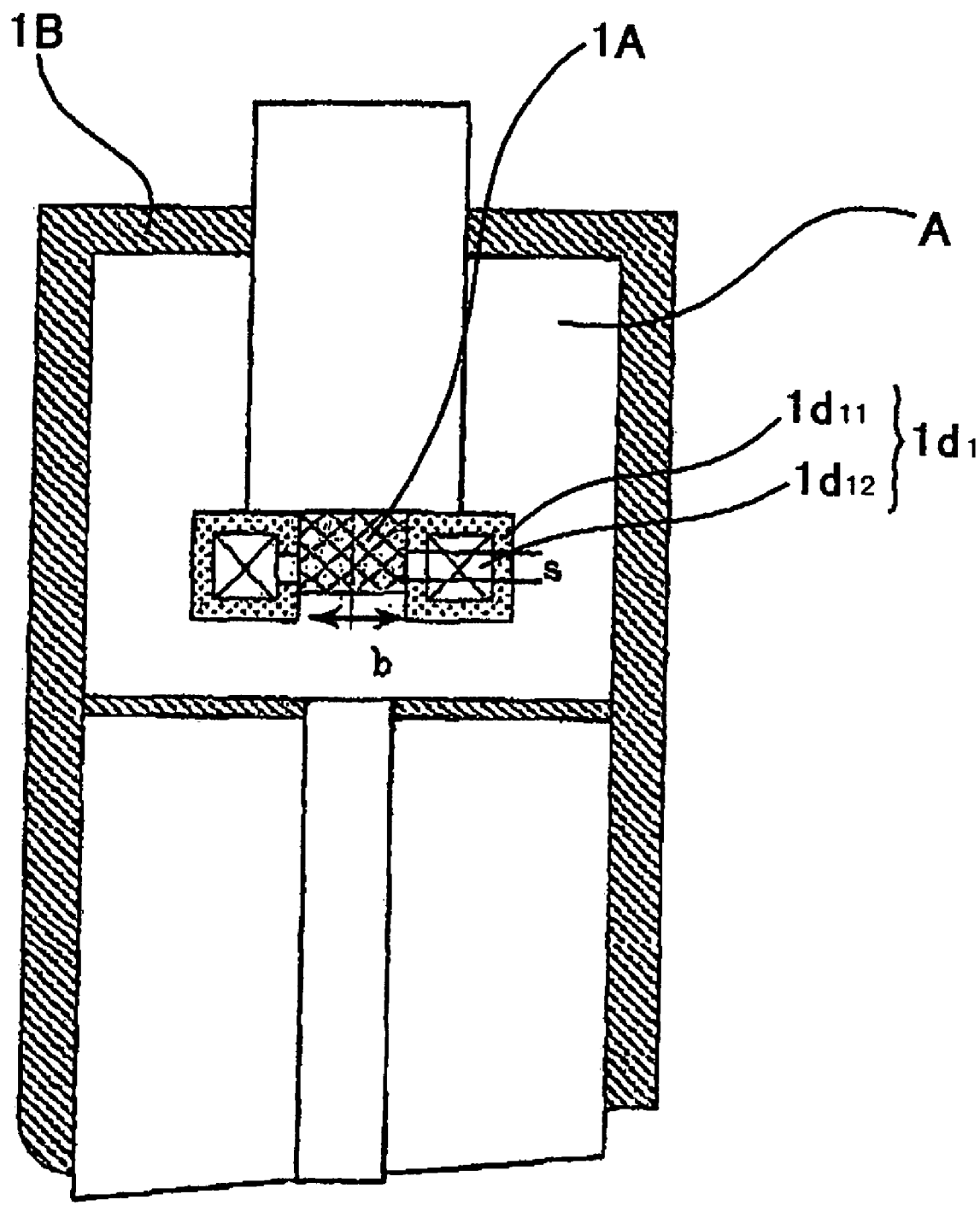
FIG. 2 is a diagram showing a construction example of a conventional FE electron gun.

However, the conventional FE electron gun has a construction in which, as shown in the construction example in FIG. 2, the entire housing of the electron gun chamber is formed from a vacuum sealing material 1B such as stainless steel, and an independent magnetic circuit $1d_1$ (magnetic body $1d_{11}$, excitation coil $1d_{12}$, etc.) is incorporated in the electron gun tip end 1A disposed within the ultra-high vacuum thereof. In such construction, there are great difficulties associated with incorporation of the magnetic circuit accompanying heat generation within the FE electron gun chamber A that requires ultra-high vacuum, cooling water, and the magnetic coil, and taking out of lead lines and pipes connected thereto. In addition, the axis alignment mechanism of the electron gun and the electron lens is also extremely difficult. On the contrary, the electron gun having the magnetic superposition lens (hereinafter, referred to as magnetic lens superposition electron gun) according to the invention has a construction in which a magnetic field generating portion of the magnetic superposition lens constituted by the magnetic circuit $1d_1$, etc. is provided in the position in the vicinity of the electron source of the electron gun (electron gun tip end 1A for generating electrons) outside the electron gun chamber under vacuum.

Figure 4:
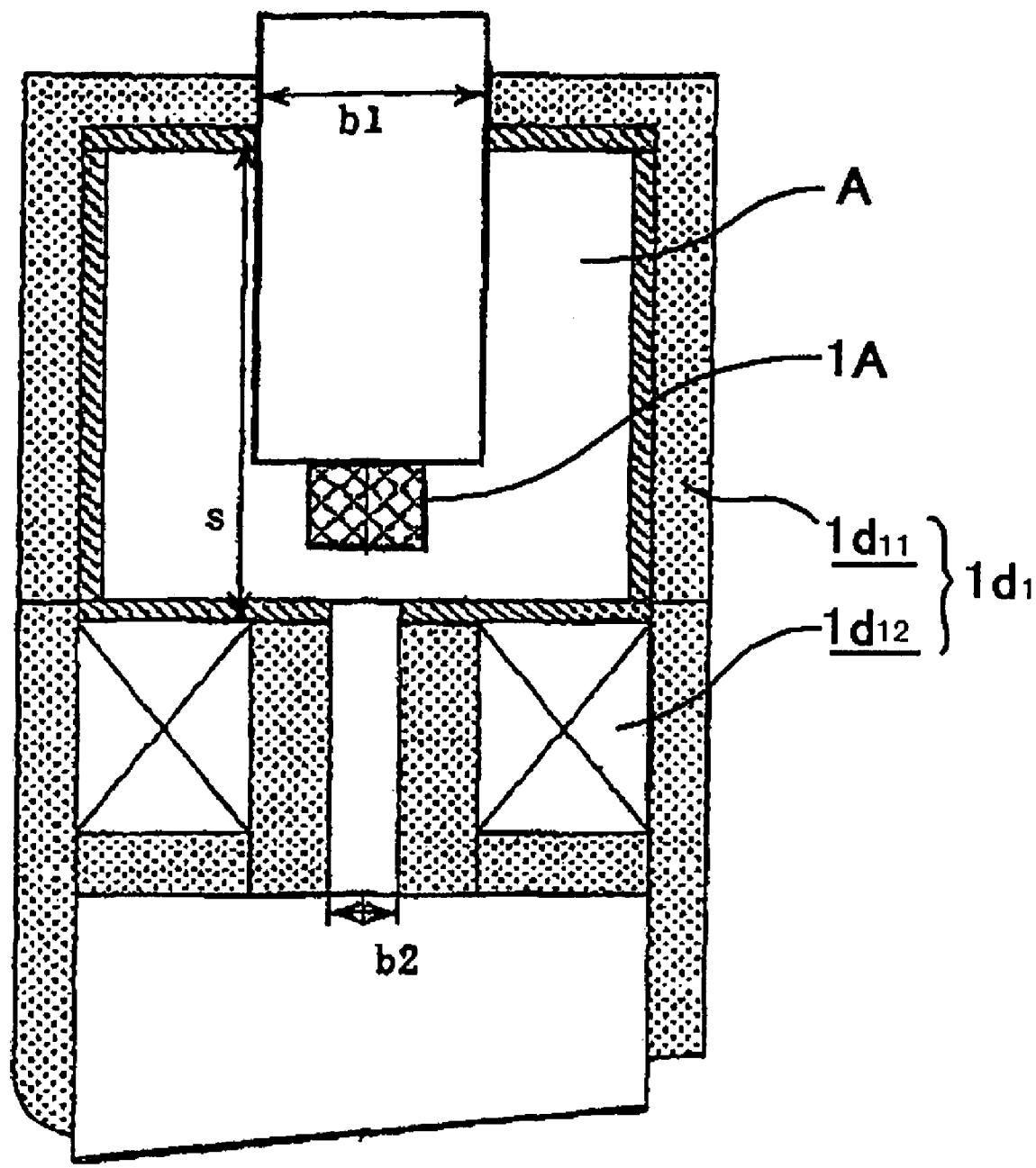
FIG. 4 is a diagram showing a first construction example of a magnetic lens superposition electron gun according to the invention.

FIG. 4 shows a first construction example of the magnetic lens superposition electron gun according to the invention corresponding to the construction of the conventional FE electron gun shown in FIG. 2. 1A denotes the electron gun tip end constituted by an emitter, a suppresser, an extractor, etc., $1d_1$ denotes the magnetic circuit, $1d_{11}$ denotes the magnetic body constituting the magnetic circuit, $1d_{12}$ denotes the excitation coil for the magnetic circuit $1d_1$, s denotes the distance between two pole pieces of the electron lens, and b2 ("b" in FIG. 2) denotes the hole diameter of the pole piece, respectively. As shown in FIG. 4, in the embodiment, the construction in which the electron gun chamber itself is incorporated in the magnetic circuit $1d_1$ constituted by the magnetic body $1d_{11}$ etc., is adopted. Specifically, the construction includes an electron gun accommodation part having a rectangular section, for example, as shown in FIG. 4, and the housing which is covered by the magnetic body as the electron gun chamber A, as the component element of the magnetic superposition lens $1d$, and the electron gun incorporated in the electron gun accommodation part. That is, the construction includes the parts of the housing (the entire or a part of the housing such as an upper plate, a bottom plate, and an outer cylinder constituting the electron gun chamber) provided as a part or the entire of the magnetic circuit (magnetic field generating portion) and the electron gun and the electron lens $1d$ separated under vacuum.

In the first construction example, strong excitation is required, since the object surface (crossover of electron source) is disposed rearward than the center of the lens field, though there is an advantage that the aberration coefficient (especially, the spherical aberration) is made significantly small. The reason for that is, generally, when the distance from the object surface (in this case, crossover of electron source) to the lower pole of the electron lens is fixed, the larger the hole diameter and the distance of the pole pieces, the smaller the spherical aberration becomes. Note that, chromatic aberration is not limited to that, the chromatic aberration can be neglected as the subject of the invention. In addition, since the magnetic circuit is separated from the electron gun chamber that requires ultra-high vacuum in construction, there is an advantage that the vacuum seal, the cooling water, and lead lines can be taken out easily.

Figure 5:
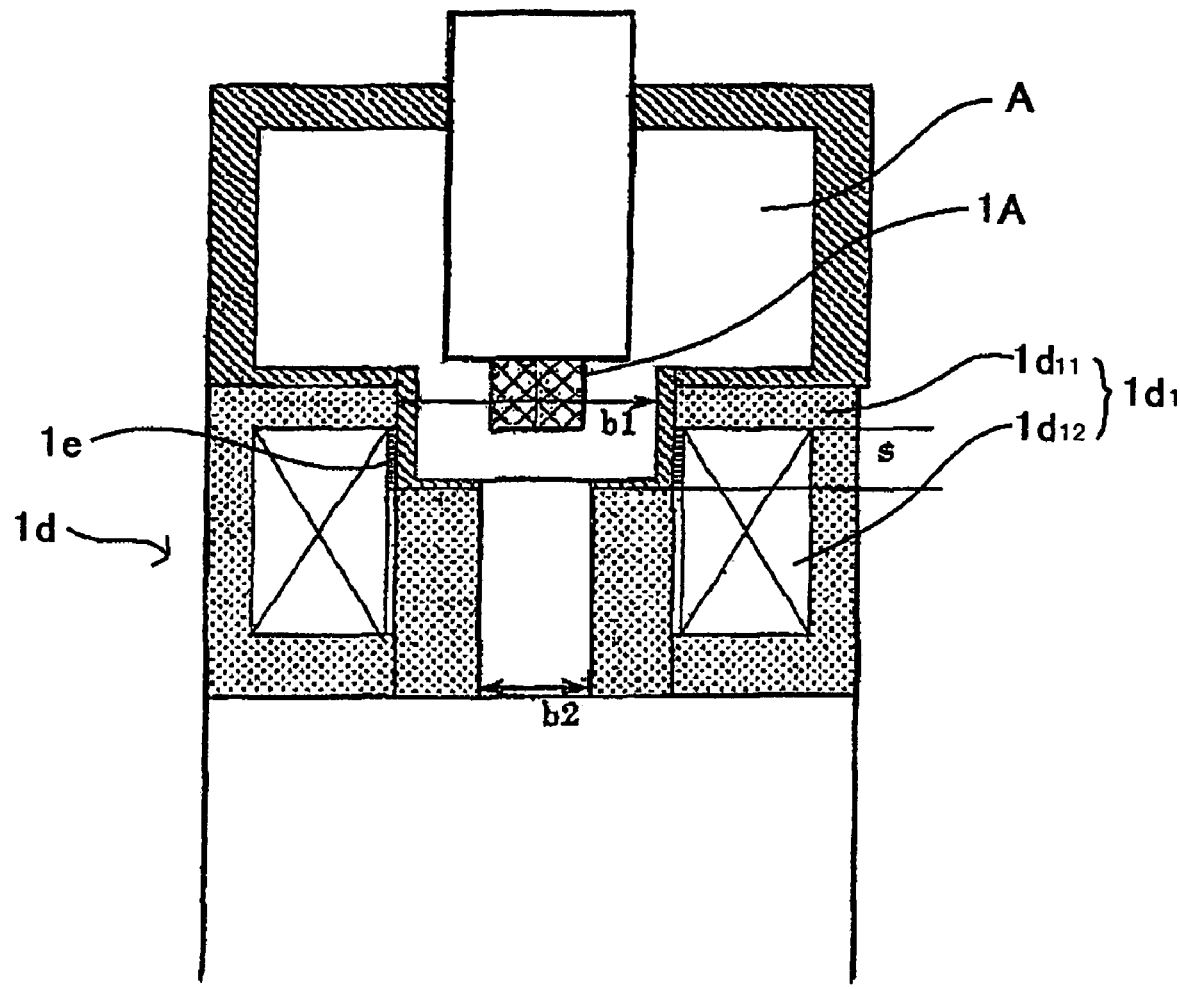
FIG. 5 is a diagram showing a second construction example of a magnetic lens superposition electron gun according to the invention.

FIG. 5 shows a second construction example of the magnetic lens superposition electron gun according to the invention corresponding to the first construction example shown in FIG. 4. In the embodiment, as shown in FIG. 5, the construction in which the electron gun chamber A in the convex form is provided above the magnetic superposition lens $1d$ constituted by the magnetic body $1d_{11}$ etc. formed so as to have a section in a concaved form, for example, and the electron gun tip end 1A is formed so as to be inserted into the magnetic field from upside of the magnetic superposition lens $1d$, so that the electron gun tip end 1A and the magnetic body $1d_{11}$ may be more close, is adopted. Since the extremely strong magnetic excitation is needed in the first construction example shown in FIG. 4, the construction is extremely effective to the low accelerated electron beams, however, not necessarily advantageous for the highly accelerated electron beams to some degree. Therefore, the embodiment adopts the construction in which the hole diameter b of the pole pieces (hole diameters b1 and b2 in different sizes between upper and lower holes in this example) and the distance s are made small so that much weaker excitation may be enough, and the electron gun tip end 1A is formed so as to be inserted into its magnetic field.

In both of the above described first and second construction examples of the magnetic lens superposition electron gun, the magnetic superposition lens has the construction in which the magnetic field generating portion is disposed in the position in the vicinity of the electron generating portion of the electron gun outside the electron gun chamber, and thereby, there are advantages that the electron gun and the electron lens are separated under vacuum (easy to realize ultra-high vacuum including baking out) and the electric field formed by the electron gun and the magnetic field formed by the electron lens are superposed with no difficulty. Further, in order to make an X-ray microscopic inspection apparatus with high resolving power in nanoscale of 40 nm to 100 nm, the X-ray microscopic inspection apparatus in FIG. 3 includes, as a component element of X-ray generating means, the electron source $1b$ using "thermal field emission cathode" or "liquid metal field emission cathode" with two orders of magnitude higher brightness than the $LaB_6$ cathode and simultaneously, with three orders of magnitude smaller size of effective electron source for the first time as the X-ray microscopic inspection apparatus. In the case of the electron source using liquid metal, the source has a construction in which the liquid metal (metal such as In (indium) and Ga (gallium) having relatively low vapor pressure at the molten state is supplied to the tip end of the electron generating portion.

Furthermore, in order to reduce the temperature rise of the target due to the electron beam and to realize that the target can endure the thermal load even if the electron beam increases largely, "target with diamond heat sink" as the target 3 for X-ray generation is provided. The diamond thin plate formed by CVD (chemical vapor deposition) has good X-ray transparency, has extremely high thermal conductivity despite that it is an insulative material and has extremely high melting point as a heat sink. A target material is deposited on the diamond by CVD and kept in the electrically conductive state to the column at the earth potential to avoid the charging up due to the insulative diamond plate.

Figure 1:
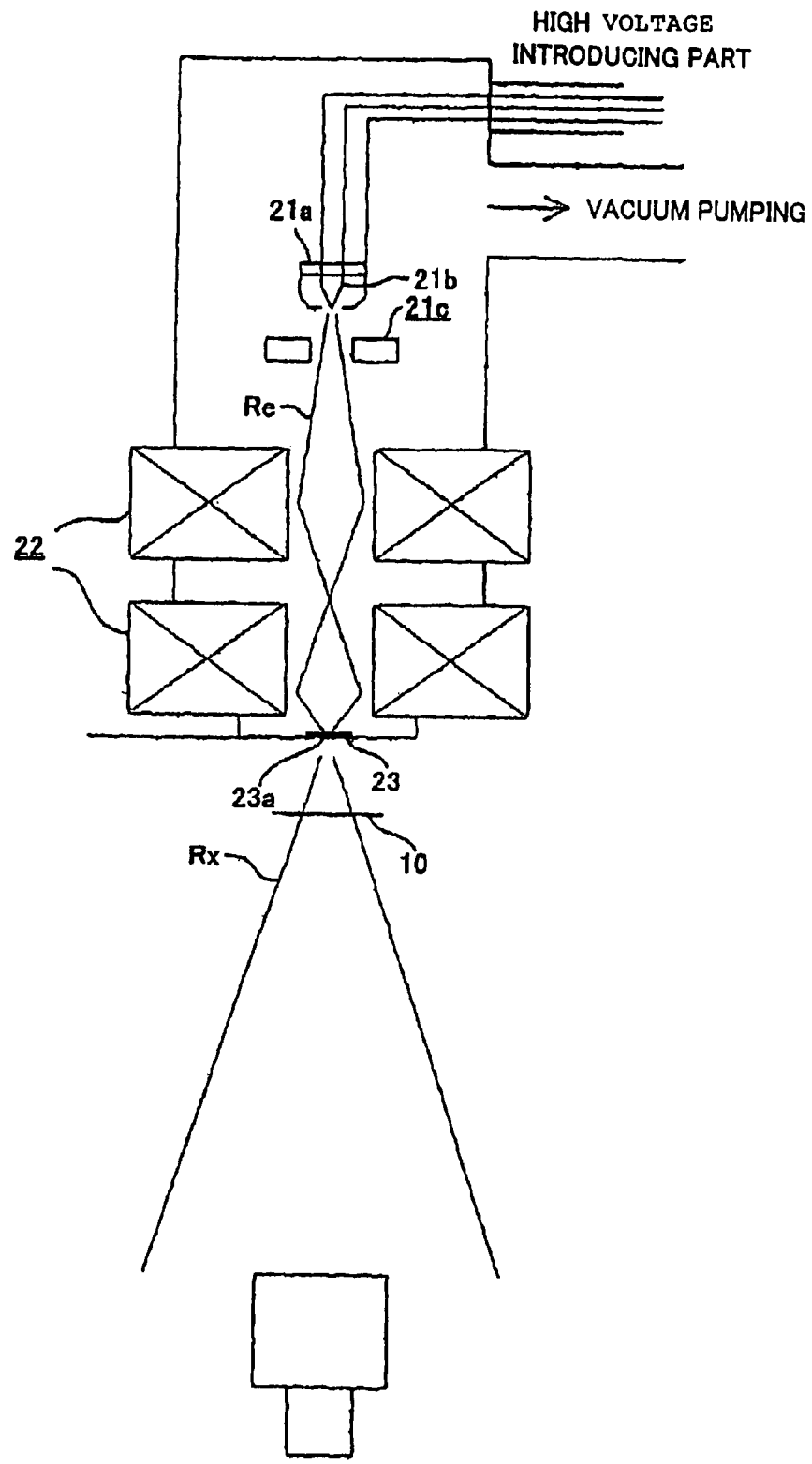
FIG. 1 is a diagram showing an example of a construction of a conventional X-ray inspection apparatus.

As an electron beam focusing lens, the above described magnetic superposition lens $1d$ only is needed principally, and the electron lens (objective lens) 2 on the target 3 side as shown in FIG. 3 is not an essential component, however, by providing the objective lens 2 to make the focusing of the electron beam into two stages, the freedom of selecting the desired electron probe size and the probe current becomes extremely increased. In addition, since the focal length of the objective lens 2 is longer as compared to that in the conventional apparatus (see FIG. 1), the longer working distance (several centimeters) that can be never obtained by the conventional X-ray microscopic inspection apparatus can be realized. On this account, the space between the objective lens 2 and the target 3 can be taken broader, and therefore peripheral equipment for the inspection can be provided within the space. In the invention, the X-ray microscopic inspection apparatus with high performance, including detection equipment, which will be described later, disposed within the above described space, capable of inspecting the microstructure of the object with high resolving power by the high density electron probe for X-ray generation, and having multiple functions never before possible is realized.

Hereinafter, the X-ray microscopic inspection apparatus having the respective functions according to the invention will be described.

The X-ray microscopic inspection apparatus has an apparatus construction in which at least one of the functions of the first to sixth functions described in "Description of the Related Art", i.e., (1) the focal point adjustment function such as focus adjustment with the reflected electron image and astigmatic correction, (2) the electron probe control function of allowing the X-ray of interest to scan the object to be inspected by swinging the electron probe freely on the target surface, (3) the electron beam axis alignment function of performing axis alignment of the electron beam allowed to impinge on the target for X-ray generation, (4) the CT function with high resolving power at high speed, (5) the elemental analysis function for analyzing the element of the desired part of the perspective image, and (6) the target switching function capable of selecting the target depending on the purpose of inspection are added. In order to realize these functions, the electron source 1b using the above described "thermal field emission cathode" or "liquid metal field emission cathode" and the target 3 with a diamond heat sink 3 are not necessarily essential as a component element, and the electron source may be an conventional electron source using the LaB6 cathode and the target may not have a diamond heat sink, however, in the embodiment, the apparatus construction including the above described component elements is adopted in order to realize an apparatus with higher resolving power.

Figure 6:
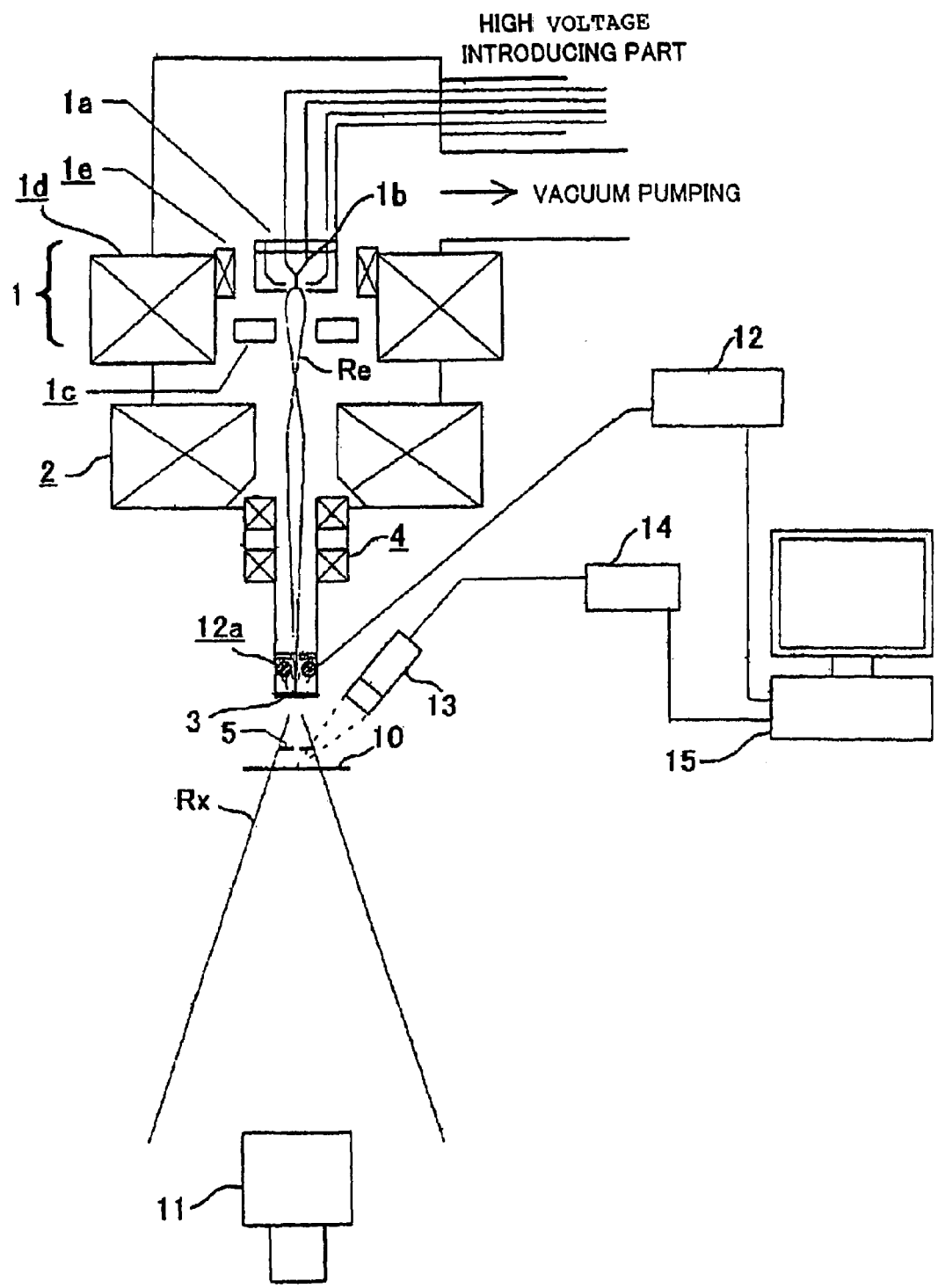
FIG. 6 is a diagram showing an example of a construction of an X-ray microscopic inspection apparatus having multiple functions and according to the invention.
Figure 7:
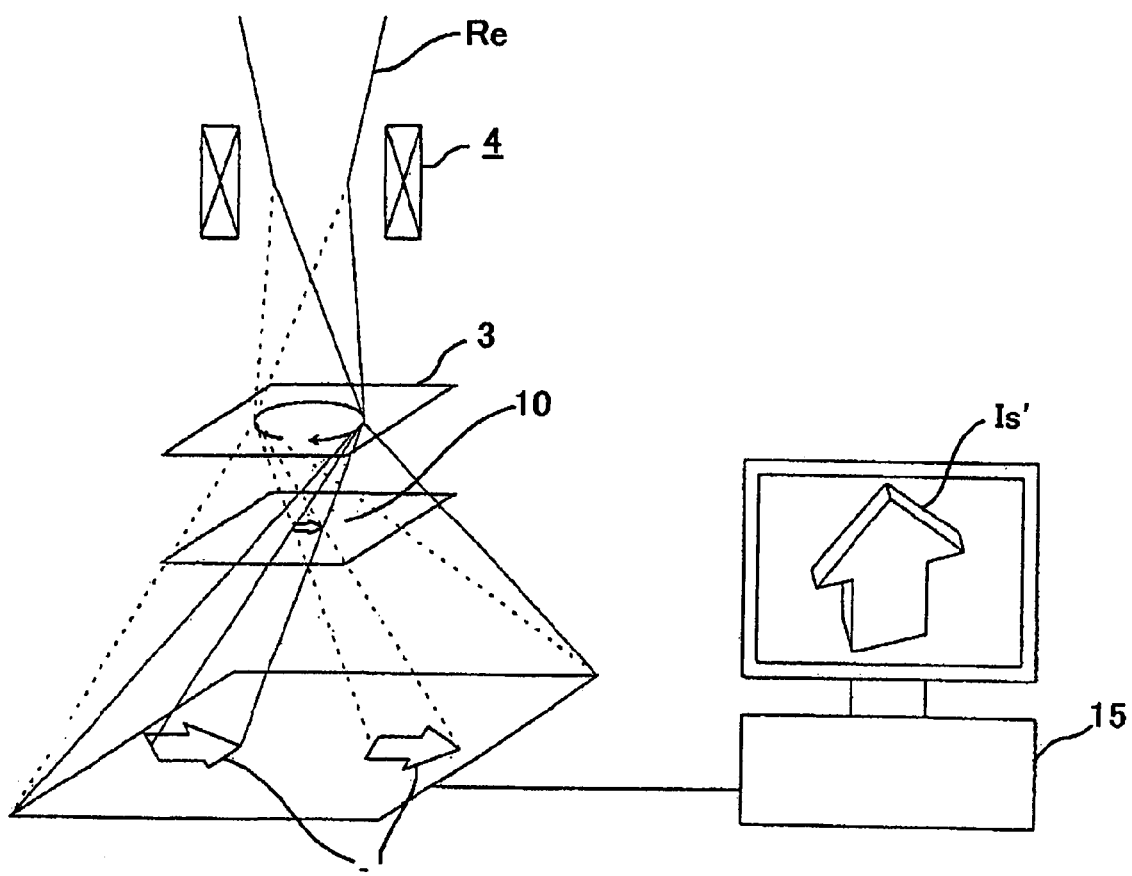
FIG. 7 is a diagram for explanation of a CT function in the invention.

FIG. 6 shows an example of a construction of an X-ray microscopic inspection apparatus having multiple functions and according to the invention corresponding to FIG. 3, and the parts having the same construction with the apparatus in FIG. 3 are assigned with the same signs and the description thereof will be omitted.

The X-ray microscopic inspection apparatus according to the invention is designed so as to be operated in a magnifying mode of several times totally while reducing the electron beam loss amount by introducing an electron lens (magnetic superposition lens) 1d for focusing electrons while accelerating the electron beam Re, as described above. Thus, the lens system is operated not in the reduction system but in the magnifying system, and thereby, the focal length of the objective lens 2 is long, and the longer working distance (several centimeters) that can never be obtained by the conventional X-ray microscopic inspection apparatus can be realized.

In the embodiment, a deflection coil (scan coil) 4 and a detecting portion of a reflected electron detector 12 constituted by a reflected electron detecting electrode 12a are provided between the objective lens 2 and the target 3, respectively. The deflection coil 4 is a coil for freely swinging the electron probe (electron beam Re) formed via the magnetic superposition lens 1d on the surface of the target 3. In this example, as shown in FIG. 6, the deflection coil 4 is formed underneath the center side of the objective lens 2.

The reflected electron detecting electrode 12a is an electrode insulated from the column for detecting the reflected electron from the target, and the detected signal of the reflected electron detector 12 is input to an analytical computer 15, in the example, and the electron image on the target surface is subjected to imaging to be displayed on the monitor.

In addition, a fluorescent X-ray detector 13 for detecting a fluorescent X-ray generated from the object to be inspected (sample) 10 is disposed above the object 10 and outside the region of the X-ray generated from the target 3. The information of the fluorescent X-ray detected by the fluorescent X-ray detector 13 is input to the analytical computer 15 via a pulse height analyzer 14, and the analysis processing of the element of the object is performed based on the detected information of the fluorescent X-ray and the preset value for identifying each element.

In the construction described above, the respective functions of the X-ray microscopic inspection apparatus of the invention will be described. The X-ray microscopic inspection apparatus shown in FIG. 6 includes the reflected electron detector 12 disposed in the vicinity of the target 3 in order to make the axis adjustment of the electron beam easily so that the electron image of the surface of the target 3 may be subjected to imaging by scanning the electron probe. Further, the apparatus is arranged so as to obtain a desired electron probe by stopping the scanning when the reflected electron image of the target 3 becomes most sharp by the adjustment such as focus adjustment (focus adjustment to the target for X-ray generation of the electron probe) and astigmatic correction of the electron probe. This method is the first trial in the X-ray microscopic inspection apparatus. This adjustment with the reflected electron image is performed by adjusting the objective lens 2 electromagnetically while watching the image that has been subjected to imaging by the analytical computer 15, for example, however, the construction in which a driving mechanism controllable by the external signal is provided and the automatic adjustment is performed based on the image information of the electron image may be adopted.

The above described scanning of the electron probe is performed by using the deflection coil (scan coil) surrounding the electron probe, and is controlled so as to scan along the predetermined path on the target for X-ray generation.

By the way, it is important that the X-ray amount applied to the sample (object to be inspected) 10 is greater in order to realize an X-ray microscopic inspection apparatus with high resolving power, and the electron beam allowed to impinge on the target 3 provides greater electron amount by a high performance lens in order to generate an X-ray with high intensity and micro focal point size, however, the orientation of the axis and the position of the electron beam are also important. In the embodiment, as illustrated in FIG. 3 and FIG. 6, the apparatus has the construction in which the electron beam axis alignment coil 1e is disposed in the vicinity of the electron generating portion 1A (close by the electron source) for the first time as the X-ray. microscopic inspection apparatus. By shifting the electron beam while acceleration to the anode 1c in X and Y directions to align the axis using the axis alignment coil 1e, the axis alignment of the electron beam can be performed precisely and easily. This axis alignment is performed concurrently with the above described focus adjustment while watching the image of the reflected electron image that has been subjected to imaging by the analytical computer 15, for example.

In the embodiment, since there is the capability of observing the reflected electron image of the target surface based on the detected signal of the reflected electron detector 12 by scanning of the electron beam (electron probe for X-ray generation), a number of images Is can be captured while swinging the electron beam Re on the target 3 by controlling the current flowing in the scan coil 4 and adding a function for allowing the electron probe to operate freely by deflecting the electron beam Re or by circular swinging on the target 3 without rotating the object to be inspected 10. Therefore, an arbitrary cross section image can be observed by the CT processing. This method can realize the CT function with several times higher resolving power at high speed because the method provides the status equal to that the object 10 is rotated extremely precisely under the condition in which the object 10 is close to the target and the high resolving power is expected.

Here, the CT image processing of X-ray images taken by the scanning of the electron probe will be described. In the embodiment, electron probe control means for scanning the electron beam focused as the electron probe on the target, and X-ray cross section image reconstruction means for allowing the microstructure of interest of the object 10 by computer processing of the plural sets of images obtained by the transmission X-ray corresponding to the circular swinging of the electron prove are provided. These controls of the electron probe and image processing are performed by the analytical computer 15 or by another control circuit and computer which are omitted here.

Figure 8:
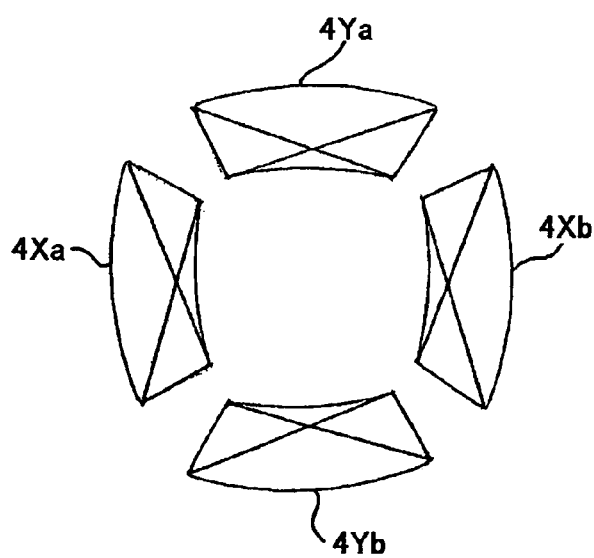
FIG. 8 is a diagram showing a construction example of a scan coil.

The scan coil 4 shown in FIG. 6 is constituted by four circular arc coils 4Xa, 4Xb, 4Ya, and 4Yb annularly disposed opposite to each other in the X and Y directions, as shown in FIG. 8, for example. Then, the current flowing in the scan coil 4 is controlled to vary the magnetic field surrounding the electron probe. Thereby, by varying the position and the orientation of the electron probe on the target in a desired direction, for example, in a circular swinging with desired speed in continuous or step by step mode and therefore their corresponding X-ray images are obtained.

Figure 9A:
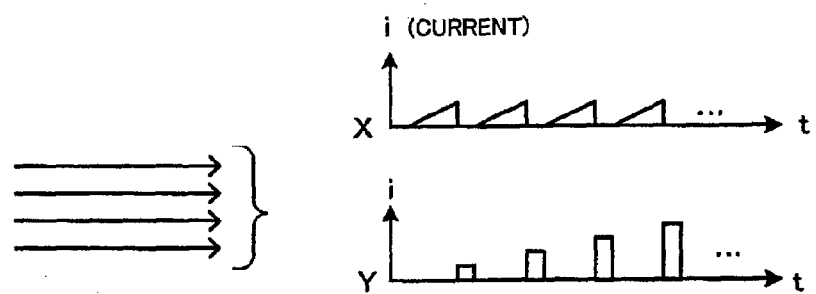
FIGS. 9A and 9B are diagrams for explanation of a control method for a scan coil for freely swinging an electron probe for scanning image of the target surface (A) and circular swinging for a new type of CT (B).
Figure 9B:
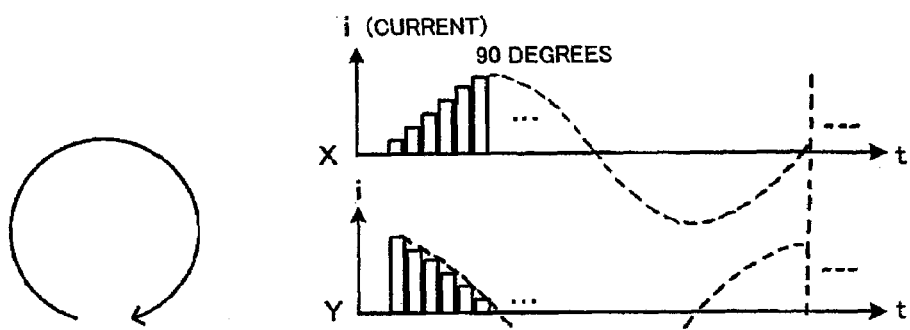

FIG. 9A schematically shows a control example of the scan coil 4 in the case where the scanning is performed by the electron probe in the horizontal direction and vertical direction. FIG. 9B schematically shows a control example of the scan coil 4 in the case where the scanning is performed in the circular swinging. As shown in FIGS. 9A and 9B, by deflecting the electron probe and continuously varying the position of the X-ray source 23a by controlling the current amount flowing in the coils 4Xa and 4Xb in the X axis direction and the coils 4Ya and 4Yb in the Y axis direction, the target 3 is scanned and the corresponding reflection electron image is obtained on the monitor and X-ray images are obtained via image intensifier 11.

Next, the elemental analysis function will be described. When an X-ray is applied to the object 10, a fluorescent X-ray having a wavelength specific to the component element of the object is generated in all directions. If this can be detected, the elemental analysis of the object can be performed. On the other hand, the continuous X-ray and the characteristic X-ray are emitted from the target 3, and specifically, the continuous X-ray is radiated downward along the incident direction of the electron. On this account, if the fluorescent X-ray detector is disposed below the object, the fluorescent X-ray can not be measured, since the continuous X-ray becomes the background. Since the X-ray microscopic inspection apparatus according to the invention has the objective lens 2 having a long focal distance and can realize the longer working distance (several centimeters): that can never be obtained by the conventional X-ray microscopic inspection apparatus as described above, as shown in FIG. 6, the space for a fluorescent X-ray analytical detector 13 can be located above the object 10 and outside of the region of the generation of an X-ray (diagonally above the X-ray target in this example).

As the fluorescent X-ray detector 13, CdTe (cadmium telluride semiconductor) etc. that can be used without cooling and has high detection sensitivity is used. A pin hole on the order of 10 to 20 μm is provided in order to specify the region of the analysis, and positional identification can be performed with the perspective image constituted by the X-ray passed through the pin hole 5 concurrently with analyzing the fluorescent X-ray scanned on the upper surface of the object and coming out upwardly.

Since the generation efficiency is higher, in the case where the fluorescent X-ray is the hard X-ray with high energy, it is necessary that the element having large atomic number is used for the analytical target. Simultaneously, it is necessary that the characteristic X-ray from the target is not confusing with the fluorescent X-ray of the object to be observed. In addition, the contrast of the image that is an important factor concurrently with the resolving power depends on the accelerating voltage and the kind of target material. The conventional X-ray microscopic inspection apparatus uses single target material, and there has been no apparatus having a mechanism utilizing various characteristic X-rays by varying the target.

Figure 10:
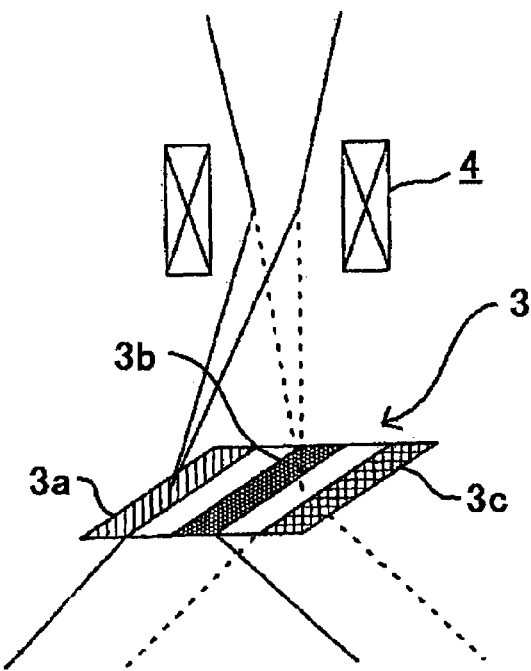
FIG. 10 is a diagram for explanation of a target switching function in the invention.

In the invention, other than W (tungsten) that has been generally and conventionally used as the target, in consideration of the target elements for fluorescent X-ray analysis of samples including light elements, high melting point metals such as Ti (titanium), Cr (chromium), Ge (germanium), Mo (molybdenum), Rh (rhodium), Re (rhenium), Ir (Iridium), and Pt (platinum) are selected as good candidates as shown in table 1. Some of them, two or three elements, are deposited on the backing material such as Be in a form of micro bands, as shown in FIG. 10, by the CVD method or sputtering method. As the function of moving the electron beam is added to the scan coil 4 immediately above the target 3, and the respective targets 3 (3a, 3b, and 3c in this example) can be selected according to the observation purpose while watching the reflected electron image. As a result, the target material that provides the optimum contrast to the each sample can be easily selected.

The following Table 1 shows the atomic numbers of these 1target materials, the wavelengths of Kα and Lα rays, and the melting points. It is seen that, from Table 1, in light of the material hardly used for the observational samples, "Rh" is suitable for the analytical target.

TABLE 1

| Symbol of element | Atomic number | Kα (nm) | Lα (nm) | Melting point (° C.) |
| --- | --- | --- | --- | --- |
| Ti | 22 | 0.275 | 2.74 | 1725 |
| Cr | 24 | 0.229 | 2.16 | 1875 |
| Ge | 32 | 0.126 | 1.05 | 937 |
| Mo | 42 | 0.071 | 0.541 | 2617 |
| Rh | 45 | 0.062 | 0.460 | 1966 |
| W | 74 | 0.021 | 0.147 | 3407 |
| Re | 75 | 0.020 | 0.143 | 3180 |
| Ir | 77 | 0.019 | 0.135 | 2410 |
| Pt | 78 | 0.019 | 0.131 | 1772 |

Note that, the X-ray microscopic inspection apparatus having all of the functions are described as an example in the above described embodiment, however, the respective functions can be provided independently.

As described above, according to the invention, the microstructure of the object to be inspected can be inspected with high resolving power by the electron probe for X-ray generation having high current density, and the X-ray microscopic inspection apparatus having multiple functions with high performance never before possible can be provided. Specifically, the adjustment including focus adjustment to the target for X-ray generation of the electron probe and astigmatic correction can be easily performed while watching the image. Further, since the electron probe can be controlled freely by the scan coil, the desired region can be inspected without rotating the object to be inspected. Furthermore, since the function of aligning the axis of electron beam while accelerating the electron is provided, the axis alignment of the electron probe for X-ray generation having high current density can be performed precisely and easily.

In addition, since the CT function with high resolving power at high speed is provided, non-destructive inspection in nano-scale such as inspection of next generation very large scale integrated circuit etc. can be performed with high precision. Further, the element of the object can be analyzed with high precision by detecting the fluorescent X-ray generated from the object without being affected by the X-ray generated from the target. Furthermore, since the different target can be selected freely depending on the purpose of inspection without exchanging it manually, the inspection with a plurality of X-rays having different wavelengths can be performed by the observation in varying contrast.

By the way, recently, the semiconductor component at the head, the miniaturization of the minimum constitutional unit is being promoted from the micro-scale to nano-scale. The non-destructive inspection of the microstructure inside of such components, the realization of the optimum contrast for each object to be inspected by utilizing the characteristic X-ray, and the elemental analysis of the micro region will be the necessary and indispensable technology in the future. Only an X-ray can be used for non-destructive inspection and analysis with high resolving power of such inner structure at the present time. Therefore, the invention can largely contribute to the nano-technology fields.

What is claimed is:

1. An X-ray microscopic inspection apparatus having X-ray generating means for generating X-rays by allowing an electron beam from an electron source to impinge on a target for X-ray generation and for inspecting an object by utilizing said X-rays, said X-ray microscopic inspection apparatus comprising:

a field emission electron gun having an ultra-high vacuum electron gun chamber, an anode and an electron generating portion, wherein the electron generating portion is adapted to generate electrons and said anode is adapted to generate an electric field to accelerate said electrons;

said field emission electron gun further comprising a magnetic superposition lens including a magnetic circuit and a magnetic field generating portion, wherein said magnetic field generating portion is disposed separately from said ultra-high vacuum electron gun chamber and said magnetic superposition lens is adapted to generate a focusing lens magnetic field having a center, wherein said magnetic field generating portion is disposed outside of said ultra-high vacuum electron gun chamber, wherein said electron source of said electron generating portion is disposed substantially in the center of said focusing lens magnetic field and said focusing lens magnetic field is superposed to said electric field thereby reducing a lens aberration of said magnetic superposition lens and reducing a loss amount of said electrons from said electron source by focusing said electrons being accelerated by said electric field, a scan coil for freely swinging an electron probe, formed via said magnetic superposition lens, on a surface of said target for X-ray generation;

said target comprising a plurality of target elements formed by a CVD method or a sputtering method, said target elements being provided for generating different characteristic X-rays having different wavelengths;

reflected electron detecting means for detecting a reflected electron from said target;

electron image generating means for performing imaging of a target surface of said target for X-ray generation utilizing signals from said reflected electron detecting means; and a target selecting means for selecting a target element by swinging said electron probe to a position of an appropriate target element by controlling a current of said scan coil, so that a characteristic X-ray having an appropriate wavelength is generated according to an inspecting purpose; and wherein said target selecting means has a function of selecting a target element within a plurality of target elements by a user's selecting operation according to an electron image of said target surface.

* * * * *